(12) United States Patent
Bharat et al.

(10) Patent No.: US 12,207,969 B2
(45) Date of Patent: Jan. 28, 2025

(54) SYSTEMS AND METHODS FOR OBTAINING MEDICAL ULTRASOUND IMAGES

(71) Applicant: KONINKLIJKE PHILIPS N.V., Eindhoven (NL)

(72) Inventors: Shyam Bharat, Arlington, MA (US); Claudia Errico, Cambridge, MA (US); Hua Xie, Cambridge, MA (US); Gary Cheng-How Ng, Redmond, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 73 days.

(21) Appl. No.: 17/776,865

(22) PCT Filed: Nov. 13, 2020

(86) PCT No.: PCT/EP2020/081988
§ 371 (c)(1),
(2) Date: May 13, 2022

(87) PCT Pub. No.: WO2021/099214
PCT Pub. Date: May 27, 2021

(65) Prior Publication Data
US 2023/0355211 A1 Nov. 9, 2023

Related U.S. Application Data

(60) Provisional application No. 62/938,491, filed on Nov. 21, 2019.

(51) Int. Cl.
*A61B 8/00* (2006.01)
*A61B 8/08* (2006.01)
(Continued)

(52) U.S. Cl.
CPC ............ *A61B 8/4245* (2013.01); *A61B 8/461* (2013.01); *A61B 8/5223* (2013.01);
(Continued)

(58) Field of Classification Search
CPC ...... A61B 8/4245; A61B 8/461; A61B 8/5223; G06T 7/0014; G06T 2207/10132;
(Continued)

(56) References Cited

U.S. PATENT DOCUMENTS 6,273,857 B1   8/2001  Aden
6,443,896 B1   9/2002  Detmer
(Continued)

FOREIGN PATENT DOCUMENTS

WO   2017010612 A1   1/2017

OTHER PUBLICATIONS

International Search Report and Written Opinion for PCT/EP2020/081988; Mailing date: Jan. 12, 2021, 9 pages.
Redmon, J. et al., "You Only Look Once: Unified, Real-Time Object Detection", arXiv:1506.02640, 2016, 10 pages.

*Primary Examiner* — Sean D Mattson

(57) ABSTRACT

A system for obtaining medical ultrasound images of a subject comprises a probe comprising an ultrasound transducer for capturing an ultrasound image, a memory comprising instruction data representing a set of instructions, and a processor configured to communicate with the memory and to execute the set of instructions. The set of instructions, when executed by the processor, cause the processor to receive an ultrasound image taken by the probe, provide the image as input to a trained model, receive from the model an indication of whether the image comprises an image relevant to a medical diagnostic process, and determine whether to bookmark the image, based on the received indication.

12 Claims, 9 Drawing Sheets

(51) Int. Cl.
    *G06T 7/00*    (2017.01)
    *G06V 10/44*   (2022.01)
    *G06V 10/82*   (2022.01)

(52) U.S. Cl.
    CPC .......... *G06T 7/0014* (2013.01); *G06V 10/454* (2022.01); *G06V 10/82* (2022.01); *G06T 2207/10132* (2013.01); *G06T 2207/20081* (2013.01); *G06T 2207/30068* (2013.01)

(58) Field of Classification Search
    CPC .......... G06T 2207/20081; G06T 2207/30068; G06V 10/454; G06V 10/82; G06V 2201/03; G06N 3/045; G06N 3/08; G06F 18/214; G16H 30/40; G16H 30/20; G16H 50/20
    See application file for complete search history.

(56) References Cited

U.S. PATENT DOCUMENTS

| | | | |
|---|---|---|---|
| 6,530,885 | B1 | 3/2003 | Entrekin et al. |
| 2014/0219548 | A1 | 8/2014 | Wels et al. |
| 2015/0305718 | A1* | 10/2015 | Ogasawara ............ A61B 8/466 600/440 |
| 2017/0262982 | A1* | 9/2017 | Pagoulatos ............ A61B 8/565 |
| 2018/0075322 | A1 | 3/2018 | Prasad et al. |
| 2018/0129782 | A1 | 5/2018 | Himsl et al. |
| 2019/0059851 | A1 | 2/2019 | Rothberg |
| 2019/0223845 | A1* | 7/2019 | Podilchuk .......... A61B 10/0041 |
| 2020/0196984 | A1* | 6/2020 | Sprung ..................... G06T 7/10 |
| 2020/0315572 | A1* | 10/2020 | Salgaonkar ............ A61B 34/20 |
| 2021/0216822 | A1* | 7/2021 | Paik ...................... G16H 30/40 |

\* cited by examiner

SYSTEMS AND METHODS FOR OBTAINING MEDICAL ULTRASOUND IMAGES

CROSS-REFERENCE TO PRIOR APPLICATIONS

This application is the U.S. National Phase application under 35 U.S.C. § 371 of International Application No. PCT/EP2020/081988, filed on Nov. 13, 2020, which claims the benefit of U.S. Provisional Patent Application No. 62/938,491, filed on Nov. 21, 2019. These applications are hereby incorporated by reference herein.

TECHNICAL FIELD

The disclosure herein relates to ultrasound imaging. Particularly, but non-exclusively, embodiments herein relate to systems and methods for recording ultrasound images.

BACKGROUND

Ultrasound imaging is used in a range of medical applications such as, for example, breast tissue examinations and fetal monitoring. Medical ultrasound imaging involves moving a probe comprising an ultrasound transducer that produces high frequency sound waves over the skin. The high frequency sound waves traverse through the tissue and reflect off internal surfaces (e.g. tissue boundaries). The reflected waves are detected and used to build up an image of the internal structures of interest.

Ultrasound imaging can be used to create two or three dimensional images. In a typical workflow, a user (e.g. sonographer, radiologist, clinician or other medical professional) may use two-dimensional imaging to locate an anatomical feature of interest. Once the feature is located in two dimensions, the user may activate a three-dimensional mode to take a three-dimensional image.

It is an object of embodiments herein to improve on such methods.

SUMMARY

In a typical workflow a sonographer may perform an ultrasound examination on a subject. Sonographers bookmark/save the images and videos that they consider to be relevant (e.g. images where a pathology is observed, or standard views for anatomy measurement). Such bookmarked images may be saved by the system for review by a more experienced radiologist who will then complete the medical diagnostic process (e.g. diagnose a particular disease or make particular measurements). Radiologists thus rely on sonographer's acquisitions when they review the images later. If the sonographer erroneously doesn't save a relevant image(s) (e.g., a small tumor), it may result in either an incomplete diagnosis or a false negative diagnosis. If the radiologist deems it necessary, the subject may have to be called back and re-scanned. This is inefficient, wasting time and resources and resulting in higher medical costs. It is therefore desirable to improve on such methods.

Thus, according to a first aspect herein, there is a system for obtaining medical ultrasound images of a subject. The system comprises a probe comprising an ultrasound transducer for capturing an ultrasound image, a memory comprising instruction data representing a set of instructions, and a processor configured to communicate with the memory and to execute the set of instructions. The set of instructions, when executed by the processor, cause the processor to: receive an ultrasound image taken by the probe, provide the image as input to a trained model, receive from the model an indication of whether the image comprises an image relevant to a medical diagnostic process, and determine whether to bookmark the image, based on the received indication.

Thus according to this method, a model may be used to determine the relevance of each ultrasound image frame to better ensure that all image frames that are relevant to the medical diagnostic process are bookmarked and saved. In this way, fewer relevant images may be missed by the sonographer, leading to improved data sets being made available to radiologists for patient diagnosis, leading to improved patient care. Furthermore this facilitates productivity improvements if diagnoses are made with increased accuracy and less need to recall subjects for repeat examinations.

According to a second aspect there is a method for obtaining medical ultrasound images. The method comprises receiving an ultrasound image; providing the image as input to a trained model; receiving from the model an indication of whether the image comprises an image relevant to a medical diagnostic process; and determining whether to bookmark the image, based on the received indication.

According to a third aspect there is a method of training a machine learning model to predict whether an image comprises an image relevant to a medical diagnostic process. The method comprises providing training data to the machine learning model, the training data comprising: i) example ultrasound images; and ii) corresponding ground truth labels, wherein the ground truth labels indicate whether the image comprises an image relevant to the medical diagnostic process. The method further comprises training the machine learning model to predict whether a new unseen image comprises an image relevant to the medical diagnostic process, based on the training data.

According to a fourth aspect there is a computer program product comprising computer readable medium comprising a computer readable medium, the computer readable medium having computer readable code embodied therein, the computer readable code being configured such that, on execution by a suitable computer or processor, the computer or processor is caused to perform the method of the second or third aspect.

BRIEF DESCRIPTION OF THE DRAWINGS

For a better understanding and to show more clearly how embodiments herein may be carried into effect, reference will now be made, by way of example only, to the accompanying drawings, in which.

DETAILED DESCRIPTION

Due to the volume and detail of the ultrasound data obtained in an ultrasound examination it isn't usually practical or desirable to save all images obtained in an examination. Thus sonographers generally bookmark (e.g. flag for saving) particular images within the examination. These are then saved and made available for a radiologist to review at a subsequent date. As described above, it is an object of the disclosure herein to provide improved workflows for obtaining medical ultrasound images of a subject in order to ensure that all images that are relevant to a medical diagnostic process or procedure are captured and thus available to the radiologist for review. This may facilitate improved diagnoses for patients and improved productivity in hospitals.

Figure 1:
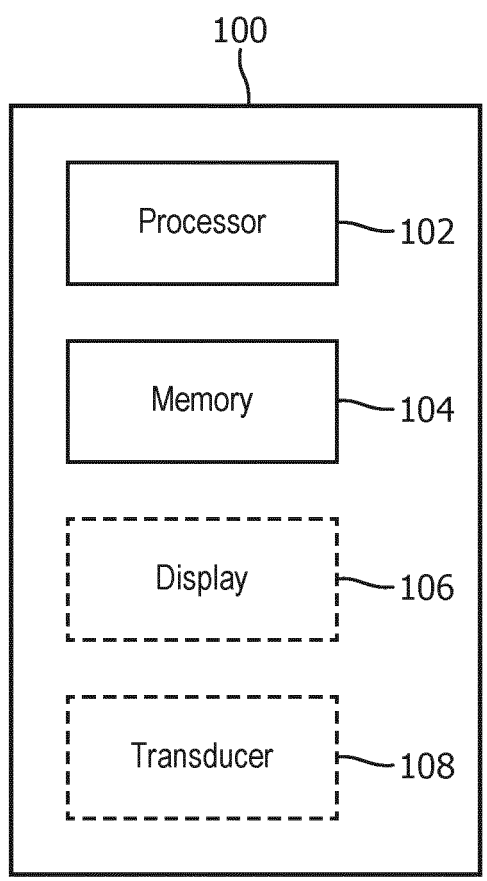
FIG. 1 illustrates an example system according to some embodiments herein.

FIG. 1 illustrates a system (e.g. apparatus) 100 for recording ultrasound images according to some embodiments herein. The system 100 is for recording (e.g. acquiring or taking) ultrasound images. The system 100 may comprise or be part of a medical device such as an ultrasound system.

With reference to FIG. 1, the system 100 comprises a processor 102 that controls the operation of the system 100 and that can implement the method described herein. The processor 102 can comprise one or more processors, processing units, multi-core processors or modules that are configured or programmed to control the system 100 in the manner described herein. In particular implementations, the processor 102 can comprise a plurality of software and/or hardware modules that are each configured to perform, or are for performing, individual or multiple steps of the method described herein.

In some embodiments, as illustrated in FIG. 1, the system 100 may also comprise a memory 104 configured to store program code that can be executed by the processor 102 to perform the method described herein. Alternatively or in addition, one or more memories 104 may be external to (i.e. separate to or remote from) the system 100. For example, one or more memories 104 may be part of another device. A memory 104 can be used to store images, information, data, signals and measurements acquired or made by the processor 102 of the system 100 or from any interfaces, memories or devices that are external to the system 100.

In some embodiments, as illustrated in FIG. 1, the system 100 may further comprise a transducer 108 for capturing ultrasound images. Alternatively or additionally, the system 100 may receive (e.g. via a wired or wireless connection) a data stream of ultrasound images taken using an ultrasound transducer that is external to the system 100.

The transducer may be formed from a plurality of transducer elements. Such transducer elements may be arranged to form an array of transducer elements. The transducer may be comprised in a probe such as a handheld probe that can be held by a user (e.g. sonographer, radiologist or other clinician) and moved over a patient's skin. The skilled person will be familiar with the principles of ultrasound imaging, but in brief, ultrasound transducers comprise piezoelectric crystals that can be used both to generate and detect/receive sound waves. Ultrasound waves produced by the ultrasound transducer pass into the patient's body and reflect off the underlying tissue structures. Reflected waves (e.g. echoes) are detected by the transducer and compiled (processed) by a computer to produce an ultrasound image of the underlying anatomical structures, otherwise known as a sonogram.

In some embodiments the transducer may comprise a matrix transducer that may interrogate a volume space.

In some embodiments, as illustrated in FIG. 1, the system 100 may also comprise at least one user interface such as a user display 106. The processor 102 may be configured to control the user display 106 to display or render, for example, portions of the received data stream or ultrasound images and/or the alert to the user. The user display 106 may comprise a touch screen or an application (for example, on a tablet or smartphone), a display screen, a graphical user interface (GUI) or other visual rendering component.

Alternatively or in addition, at least one user display 106 may be external to (i.e. separate to or remote from) the system 100. For example, at least one user display 106 may be part of another device. In such embodiments, the processor 102 may be configured to send an instruction (e.g. via a wireless or wired connection) to the user display 106 that is external to the system 100 in order to trigger (e.g. cause or initiate) the external user displays to display the alert to the user to indicate that the feature of interest is in view of the user.

It will be appreciated that FIG. 1 only shows the components required to illustrate this aspect of the disclosure, and in a practical implementation the system 100 may comprise additional components to those shown. For example, the system 100 may comprise a battery or other means for connecting the system 100 to a mains power supply. In some embodiments, as illustrated in FIG. 1, the system 100 may also comprise a communications interface (or circuitry) 108 for enabling the system 100 to communicate with any interfaces, memories and devices that are internal or external to the system 100, for example over a wired or wireless network.

Briefly, the processor 102 is configured to: receive an ultrasound image taken by the transducer 108 in the probe, provide the image as input to a trained model, receive from the model an indication of whether the image comprises an image relevant to a medical diagnostic process, and determine whether to bookmark the image, based on the received indication.

As will be described in detail below, embodiments herein use models, such as deep learning models (e.g. neural networks) to determine which ultrasound images or views are relevant to the medical examination being performed. Images deemed relevant by the model may then be saved (in addition to any images flagged by the user/sonographer as being relevant). This augments manually-saved ultrasound image collections by also automatically saving relevant images that may have been missed by the user. Such a deep learning system can, in the training phase, learn image "relevance" from training on breast image data acquired and labelled by highly skilled sonographers/clinicians as relevant or not relevant. As will also be discussed below, probe position may be added as an optional input parameter to the model to further augment the image classification process. Some embodiments described herein further provide methods of displaying relevant images and their locations within the body to the user. For example, to improve the ability of a user to find a suspicious portion of tissue in a subsequent examination. Training and using a model in this way provides improved workflows to ensure improved image capture and improved subsequent diagnoses and patient care.

In more detail, herein, references to a subject refer to a patient or other person who the ultrasound imaging is performed on. References to a user may comprise the person, e.g. clinician, doctor, sonographer, medical professional or any other user performing the ultrasound examination.

Generally when an ultrasound examination is performed, it is performed for a particular purpose, referred to herein as a (particular) medical diagnostic process. Examples of medical diagnostic processes include a breast examination looking for anomalous breast tissue or breast lesions; a vascular examination of one of the extremities of the subject (hands, fingers, toes etc), or a thyroid ultrasound examination. In some examples, a medical diagnostic process may be performed according to a medical guideline, for example, the medical diagnostic process may comprise a fetal examination where particular parts of the foetus should be imaged in accordance with a medical guideline for fetal examinations. The skilled person will appreciate that these are merely examples however and that the embodiments described herein may be applied to a wide range of ultrasound medical diagnostic processes.

Herein the term relevance is used to describe whether an image is relevant to the medical diagnostic process being performed. Relevant may describe whether a sonographer would class an image as useful, helpful, necessary, required or otherwise pertaining to the medical diagnostic process being performed. An image may be relevant to a medical diagnostic process to determine whether a patient has cancer, if it shows anomalous tissue such as a lesion, for example. Conversely, an image may also be relevant to a cancer diagnosis if it demonstrates that an entire anatomical feature is anomaly free. In this sense therefore, an image may be deemed relevant if it would be used by a clinician to make a diagnosis or otherwise perform the medical diagnostic process.

The trained model may comprise any model that may take an ultrasound image as input and provide as output a classification or prediction of whether an image is relevant to a medical diagnostic process e.g. whether it would be used by a user/clinician to perform the medical diagnostic process.

For example, the model may comprise a model trained using a machine learning process, such as a deep learning process. In some embodiments the trained model may comprise a trained neural network or deep neural network. Examples of appropriate neural networks include but are not limited to convolutional networks such as a trained F-net or a trained U-net.

The skilled person will be familiar with neural networks, but in brief, neural networks are a type of supervised machine learning model that can be trained to predict a desired output for given input data. Neural networks are trained by providing training data comprising example input data and the corresponding "correct" or ground truth outcome that is desired. Neural networks comprise a plurality of layers of neurons, each neuron representing a mathematical operation that is applied to the input data. The output of each layer in the neural network is fed into the next layer to produce an output. For each piece of training data, weights associated with the neurons are adjusted until the optimal weightings are found that produce predictions for the training examples that reflect the corresponding ground truths.

In embodiments wherein the trained model comprises a neural network, the neural network may comprise a convolutional neural network like a U-net or an F-net suitable for classifying an image according to relevance. The trained model may take as input an ultrasound image and provide as output an indication of whether the image comprises an image that is relevant to the medical diagnostic process being performed. The indication may comprise a binary classification ("relevant" or "not-relevant"), a graded classification (e.g. on a scale), a likelihood or percentage likelihood of relevance or any other indication of whether the image is relevant (or not).

In some embodiments a siamese neural network may be used. In brief, a Siamese network is a convolutional neural network (CNN) that leverages the use of same weights while working simultaneously on two separate inputs. Usually, they output a score of similarity between the two inputs. For instance, herein Siamese networks may be used to distinguish between images already captured or bookmarked by a user and those that should be added to the auto-save list, in order to avoid redundant information (redundant image capture).

In some embodiments the trained model has been trained to provide the indication of whether the image comprises an image relevant to the medical diagnostic process based on training data comprising: i) example ultrasound images and ii) corresponding ground truth indications of whether each example ultrasound image comprises an image relevant to the medical diagnostic process.

Figure 2:
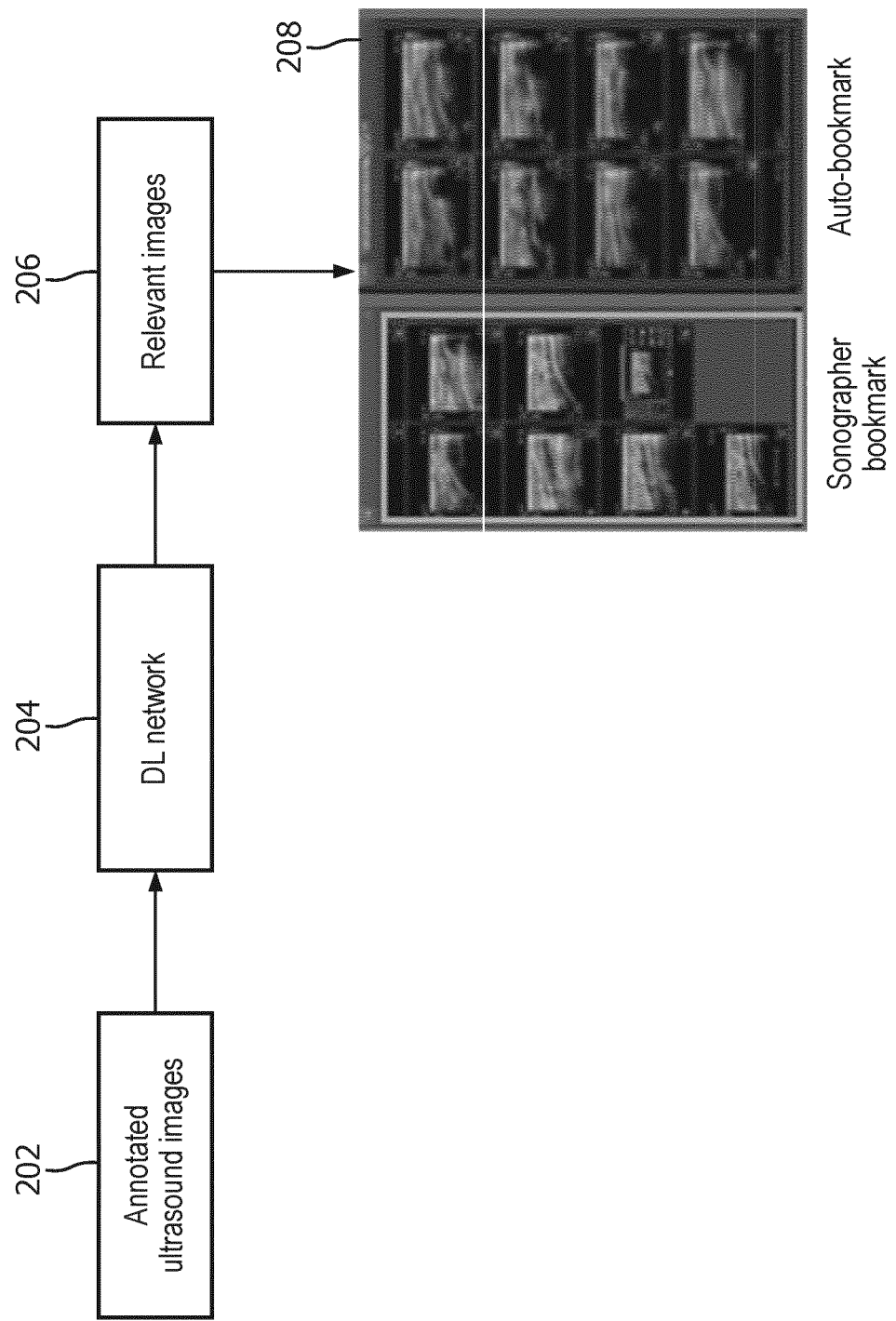
FIG. 2 illustrates an example method according to some embodiments herein.

This is illustrated in FIG. 2 which shows training data 202 comprising annotated ultrasound images being provided as input to a deep learning neural network model 204. The annotations comprise the ground truth indications of whether each example ultrasound image comprises an image relevant to the medical diagnostic process. The annotated ultrasound images are provided to deep learning neural network 204 which is trained, using the training data, to predict of whether an image comprises a relevant image 206 (e.g. relevant to the medical diagnostic process) based on the annotated ultrasound images 202.

Generally, the training data (e.g. ultrasound image frames) may be collected from a wide range of available ultrasound systems and labelled by expert sonographers and clinicians with clinical annotation. The images, classified as "relevant", may be input of the deep learning network which is trained to learn the features of "relevant" images. To improve training accuracy, additional images may be gathered that would not be saved in a typical clinical scan session by expert sonographers (e.g. examples of "not-relevant" images). The advantage of training on all images (and not just on relevant saved images) is that the system learns not only which ones are "relevant" images that need to be saved, but also the images that do not need to be saved. This way, the network may be able to better predict both images missed and saved by the sonographer. Furthermore, by training the model on a training data set compiled (annotated) by more than one sonographer, the expertise of many different sonographers may be used to train the model. Effectively the model may therefore combine the expertise of all of the sonographers who contributed to the training data set when determining whether an image is relevant or not relevant, which may be advantageous compared to a single sonographer manually classifying images thus.

Once the model is trained, in inference, the deep learning neural network may be used to predict whether a new (e.g. unseen) image is relevant to the medical diagnostic process. During inference (live scan), the network can run in the background. If a suspicious image is not bookmarked by the sonographer, the system can thus automatically capture it. Images classed as relevant may be bookmarked by the system and displayed to the user. Images may be displayed in groups, for example, according to whether the image was bookmarked by the user or bookmarked by the system (due to the relevance classification) as shown in the pane 208 in FIG. 2.

Turning back to FIG. 1, in some embodiments, the processor 102 is further caused to determine a location on the body of the subject associated with the position of the probe when the image was captured.

The location may be determined in various ways. For example, the transducer 108 may be integrated with an electromagnetic (EM) sensor, that can be tracked within an EM field that is generated by, for example, a table top field generator fused with the patient table. The recorded locations may be calibrated, for example with reference to particular features. For example, in a breast examination, the sonographer may calibrate the location by indicating to the system the location of the nipple. Such an EM tracking feature allows coupling of B-mode images with probe position to provide visual mapping of the exam.

It will be appreciated that this is an example however and that the location of the probe (transducer) on the body may be determined in other ways, including but not limited to a motion detector in the probe or one in which the probe position is determined using optical tracking (calibrated in a similar manner to that described for the EM sensor).

In some embodiments, the set of instructions, when executed by the processor, further cause the processor to provide the determined location on the body as a further input to the trained model. Put another way, in some embodiments, the trained model is further trained to provide the indication of whether the image comprises an image relevant to the medical diagnostic process based on the determined location. As such, "relevance" may be decided based on two factors (e.g. inputs): (i) The image, and (ii) The probe position.

For example, if the system decides that a certain image is relevant, it may bookmark it and also save its position. Subsequently, the user may continue to maneuver the probe around that area, looking for more "relevant" images to bookmark. Say the user then reaches a probe position that is orthogonal to the originally bookmarked probe position. Even if the "relevance" of this image is borderline (e.g., not obviously relevant) from the image features itself, the model may still determine that the image is relevant (and thus should be bookmarked), because the probe position indicates that this image should represent another slice through the object of interest (e.g., tumor).

Figure 3:
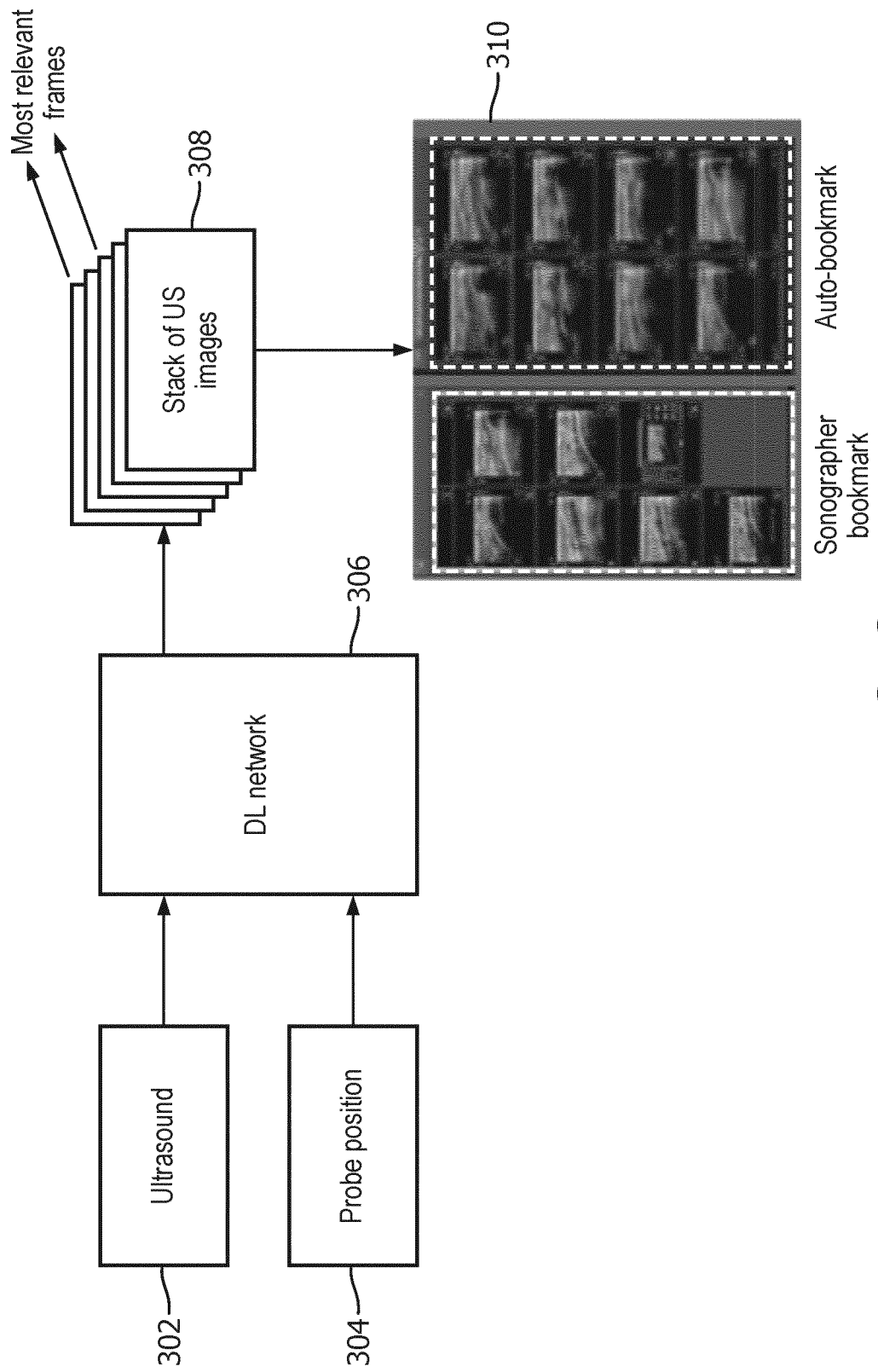
FIG. 3 illustrates an example method according to some embodiments herein.

This is illustrated in FIG. 3 which shows training data comprising ultrasound images 302 and corresponding probe positions 304 being provided as input to a deep learning neural network model 306. Deep learning neural network 306 is trained to predict an indication of whether the image comprises a relevant image 308 (e.g. relevant to the medical diagnostic process) based on the ultrasound images 302 and probe positions 304.

In this approach, where probe position along with B-mode ultrasound images are input to the deep neural network, the deep learning network can decide across adjacent frames (in short time and in space) which one is the most relevant and intelligently select which one to auto-capture avoiding redundant information to the sonographer. Images along with clinical annotations and probe positioning may be utilized as labels to train the deep learning network. This training approach leverages the meaningful information contained in a stack of ultrasound images and—for example—in given a sequence of five frames, the deep learning network may be able to pick the most relevant image frame(s) to save. In some embodiments, the network may output a score for each image frame, which classifies the best image frame to capture. Similarity across image frames can be learned though salient features of the frames and through pose information.

It is further envisioned that a 3D deep learning network may be able to smartly reconstruct a 3D volume from a sweep, for example of a breast, and select the suspicious planes to auto-capture relevant frames. This training option may be useful for a 3D deep learning network used in breast examinations, where the whole volume of the breast may be captured.

Since each frame is labelled with its relative probe position, a deep learning network may also be trained to a) reconstruct the whole volume given the probe position, and b) determine which planes are relevant and bookmark the relevant frames within the stitched volume.

Figure 4:
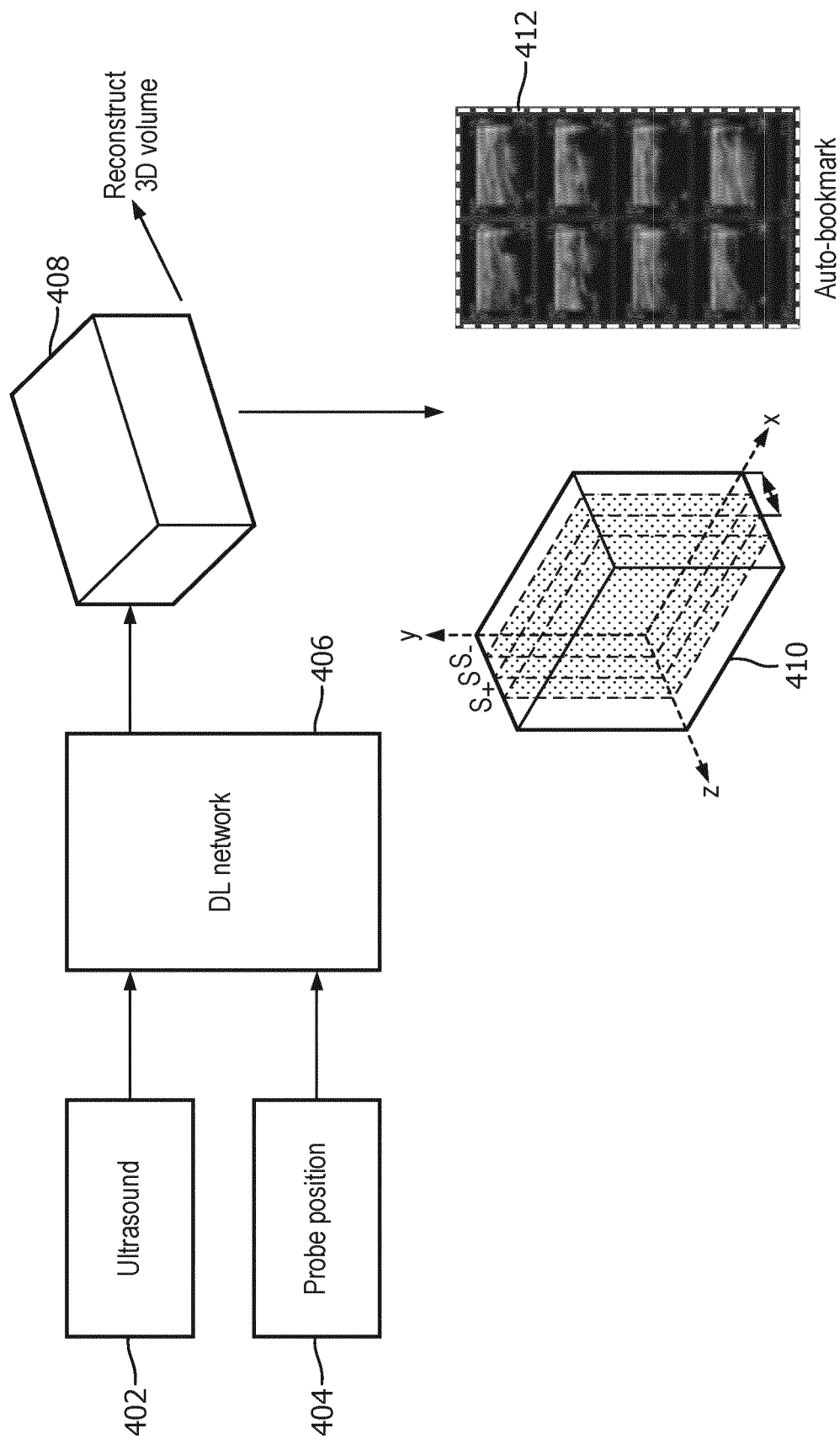
FIG. 4 illustrates an example method according to some embodiments herein.

This is illustrated in FIG. 4 whereby a Deep learning neural network 406 takes as input a plurality of ultrasound images 402 and corresponding probe positions 404 and outputs a reconstructed 3D volume 408 whereby each slice through the 3D volume is labelled according to relevance 410. In inference, the location of relevant frames may be highlighted/displayed to a user using a graphic such as the graphic 412.

The skilled person will be familiar with methods of training a neural network using training data (e.g. gradient descent etc.) and appreciate that the training data may comprise many hundreds or thousands of rows of training data, obtained in a diverse range of network conditions.

Generally, it is noted that training and validation datasets may be improved if they comprise images from a diverse set of examinations comprising different diagnostic findings that a sonographer would want to save, and a large population of patients with different tissue properties. The training data may further be improved if the training images are obtained from ultrasound examinations performed and annotated by different expert users. This may better capture inter-user variability and as noted above, result in a model that effectively combines the expertise of many sonographers, over many different tissue types.

Once the model is trained, in inference, the deep learning neural network may be used to predict whether a new (e.g. unseen) image is relevant. Images classed as relevant may be bookmarked by the system and displayed to the user, for example, according to whether the image was bookmarked by the user or bookmarked by the system (due to the relevance classification) as shown in the panes 310 in FIGS. 3 and 412 in FIG. 4.

Thus in summary, relevance may be determined solely from the images. In such examples, probe position may be stored in parallel, for easier user interpretation of the bookmarked image. Alternatively, relevance may be determined from the image and the probe position.

The skilled person will further appreciate that other inputs may also be provided to the model, in addition or alternatively to the examples provided herein.

Furthermore, the model may be trained to have other output channels. For example, in some embodiments, the model may further output a suggestion to the user of a further location that the user may want to scan. For example, in a breast examination, a sonographer may decide whether or not to scan the axillary lymph nodes (closer to the arm pit) in order to check for the presence of metastases. The system can also be trained to perform this task, where, based on the images considered "relevant" and captured in the earlier embodiments, the system can suggest the user scan the axillary lymph nodes.

It will be appreciated that alternatively, the system may provide a further location to the user, for the user to perform a further scan, based on the indication(s) received from the model.

Once the probe has been appropriately positioned for axillary lymph node scanning, the "relevant" images can be saved here as well (and annotated separately).

Furthermore, it will be appreciated that although examples herein describe the use of neural networks, any model may be used that may take the inputs described above and output an indication of whether an image is relevant to a medical diagnostic process. Examples include but are not limited to random forest models.

Once the processor has received an ultrasound image taken by the probe; provided the image as input to a trained model; and receive from the model an indication of whether the image comprises an image relevant to a medical diagnostic process, as described above, the processor is then caused to determine whether to bookmark the image, based on the received indication.

In some embodiments, the processor is further caused to determine whether the image has been selected by a user as an image to be bookmarked (manually bookmarked). The processor may then determine to bookmark the image if the image has not been selected by the user as an image to be bookmarked and if the received indication from the trained model indicates that the image is relevant to the medical diagnostic process. In other words, if the model determines that the image is relevant, but it isn't selected to be bookmarked by the user (sonographer) then the system may determine to book mark the image independently of the sonographer.

Bookmarked images may be recorded (e.g. tagged) according to whether they were bookmarked by the user or by the system, e.g. due to them being classified by the model as relevant. Such tags may be used by the system when displaying the images to the user.

For example, the processor may send an instruction to a display to display the image to the user, and further indicate to the user whether the image has been i) selected by a user as an image to be bookmarked or ii) bookmarked by the system based on the received indication from the trained model.

Images may be grouped according to whether they were manually bookmarked or book marked by the system, and displayed in different panes, as was described above and illustrated by reference numerals 208 in FIG. 2, 310 in FIGS. 3 and 412 in FIG. 4.

Figure 5A:
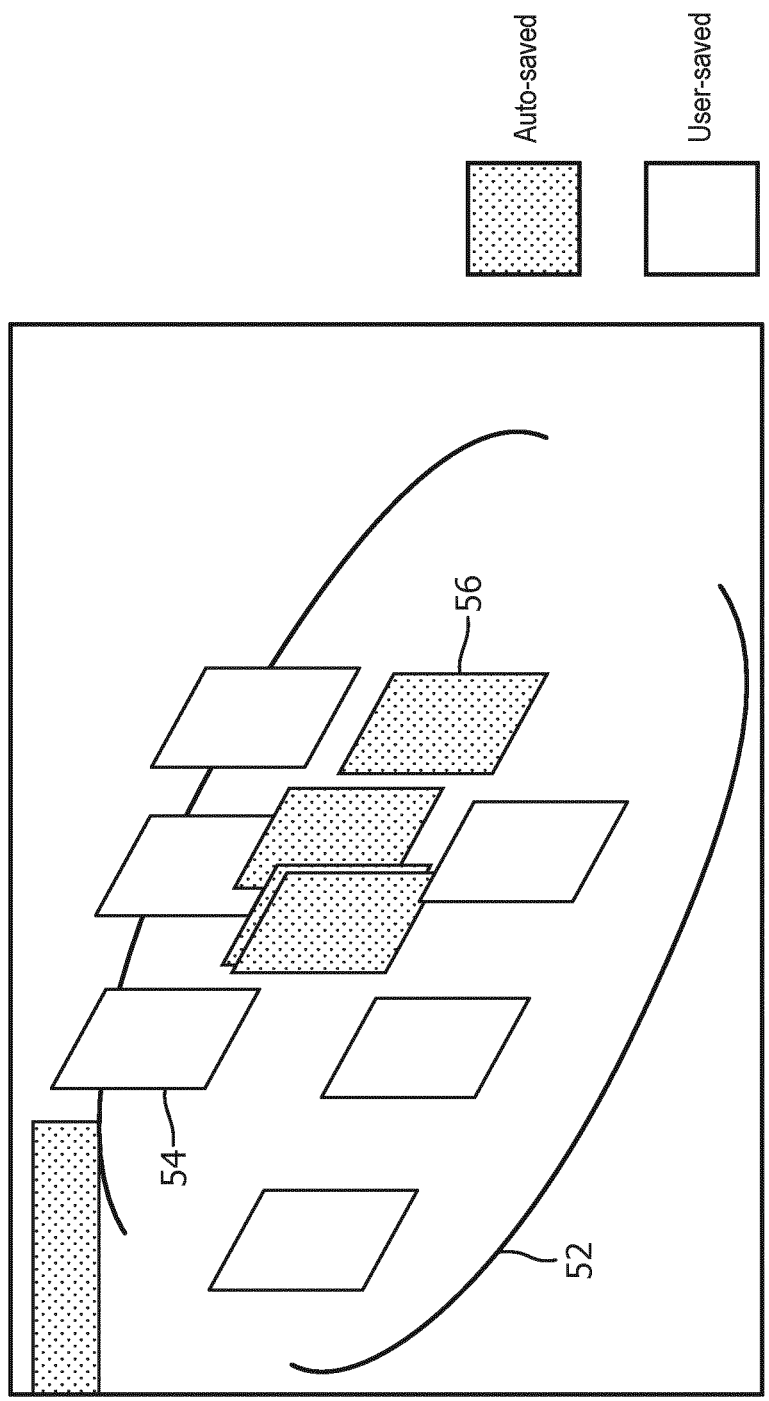
FIGS. 5a, 5b and 5c illustrate example displays according to some embodiments herein.

Furthermore, images may be grouped and/or displayed according to their location on the body. An example is illustrated in FIG. 5*a* which shows a schematic representation of a breast 52, overlain with the locations of the ultrasound images that have been taken. Each indicated ultrasound image may be color-coded according to whether the image was bookmarked by the user or sonographer 54, or bookmarked by the system 56.

Turning now to other embodiments, the processor may be further caused to determine a location on the body of the subject associated with the position of the probe when the image was captured and send an instruction to a display to display an indication of the determined location on the body to the user. This may be performed for each image that is classed as relevant by the model.

Figure 5B:
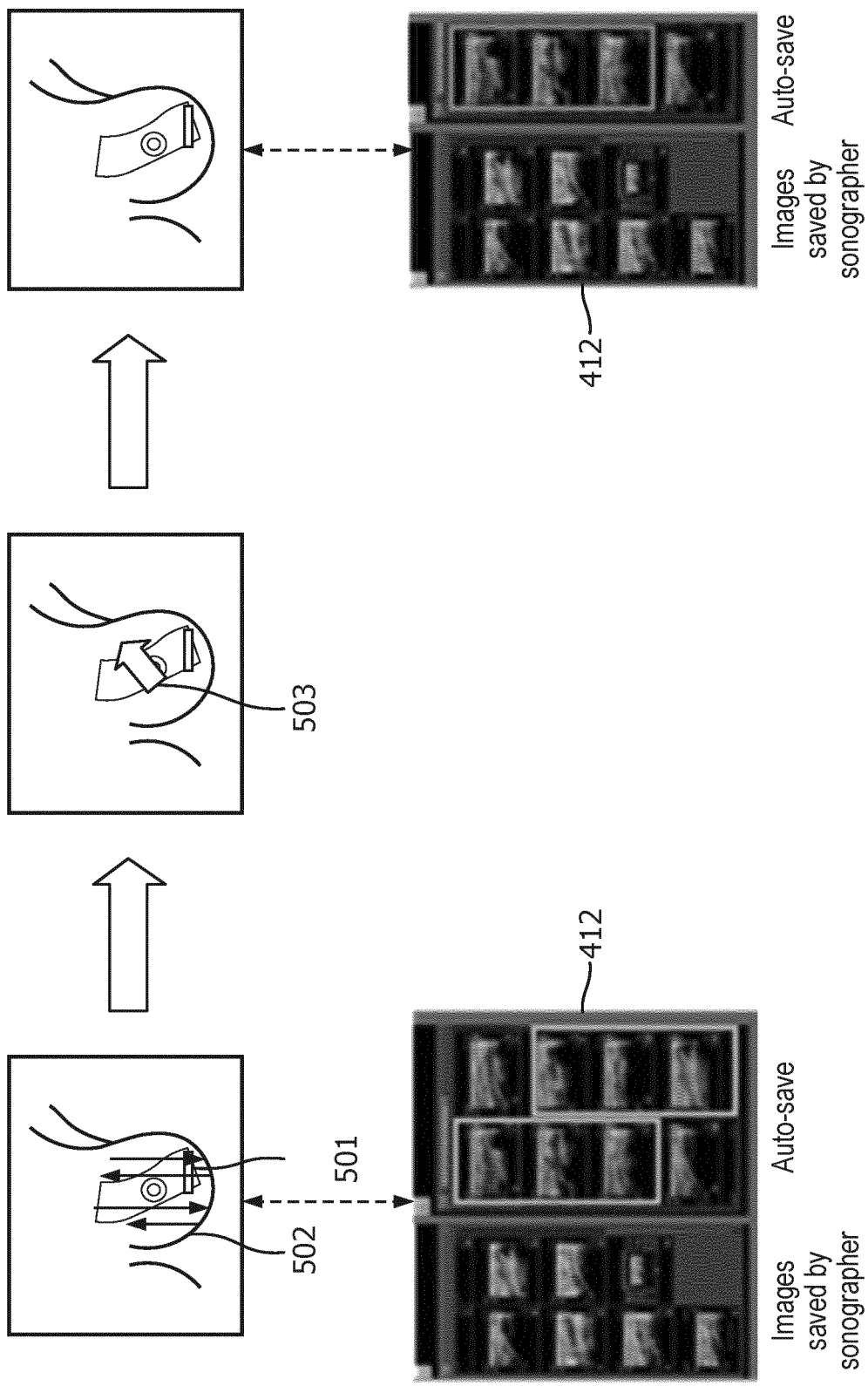

In the example shown in FIG. 5*b*, the medical diagnostic process comprises a breast examination and the body part comprises a breast. In this embodiment the processor is caused to display a schematic representation of a breast 502. During the examination, the location of the probe (and/or previous locations of the probe) may be indicated by means of a line or trail 501. If an additional output channel is provided that provides a suggestion of another location on the breast at which imaging may be performed, this may be indicated, for example by arrow 503 which provides an indication of a direction that the probe should be moved in. The different frames may be presented in groups 412 as described above.

In more detail, the processor may be caused to send an instruction to the display to display a representation of a body part and overlay the indication of the determined location on the body over the representation of the body part. For example, a cartoon or other schematic of a body part may be displayed. The locations of relevant images may be represented as pin-points, bullet points, dots, crosses or any other means of representing a location on a representation of a body part.

Figure 5C:
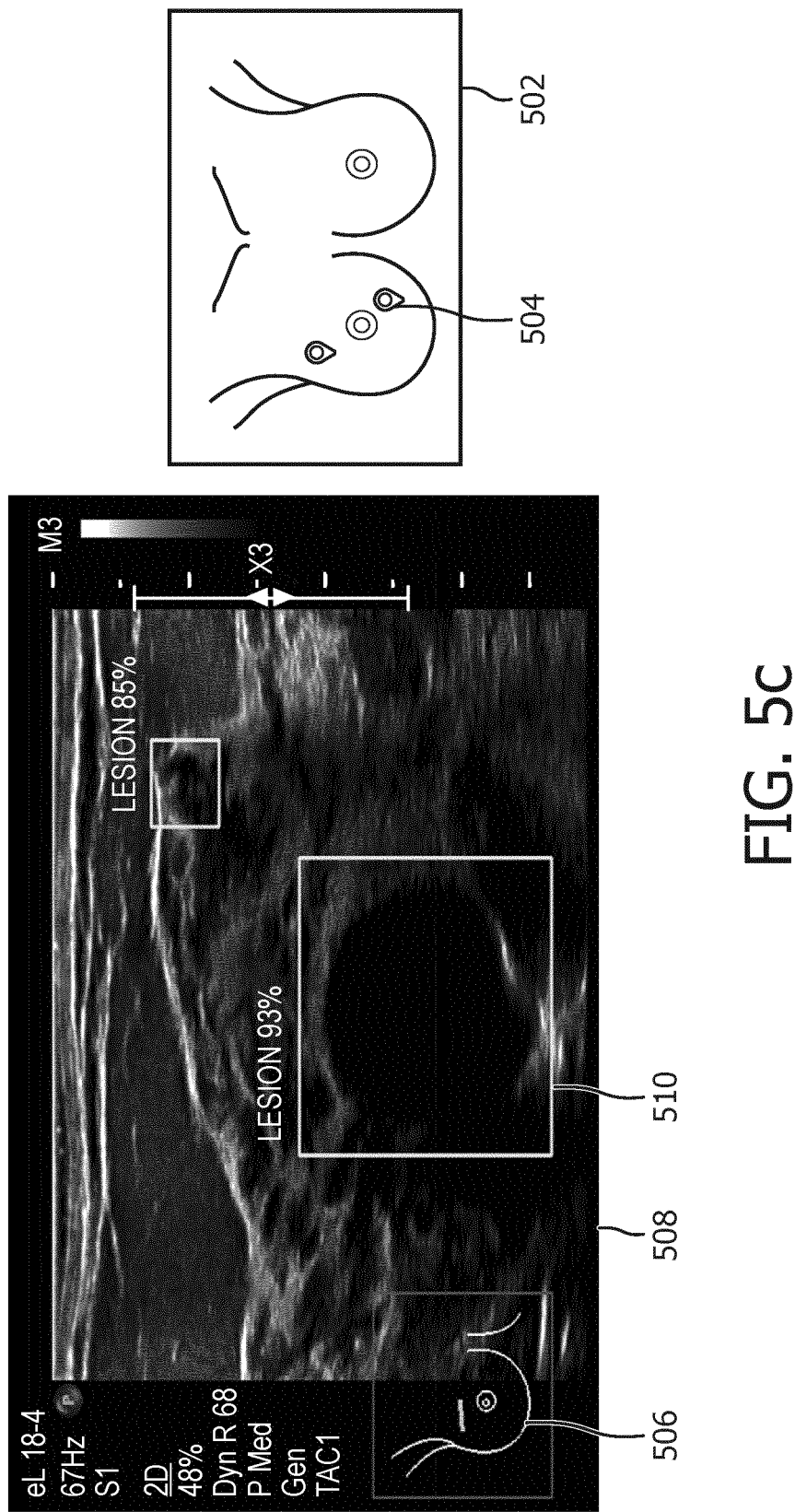

In the example shown in FIG. 5*c*, the medical diagnostic process comprises a breast examination and the body part comprises a breast. Thus the processor is caused to display a schematic representation of a breast 502. Overlain on the representation of the breast are icons indicating the locations of image frames that were determined by the model as being relevant to the medical diagnostic process of the breast examination.

Such graphics may be used in a subsequent (e.g. follow up) ultrasound scan to aid the sonographer to locate the relevant image locations more easily. For example, the processor may be caused to receive a subsequent real-time sequence of ultrasound images (e.g. from a subsequent scan) and send an instruction to the display to display an indication of the position of the probe when each ultrasound image in the subsequent real-time sequence of ultrasound images was captured, compared to the position of the probe when the image was captured. This may aid the sonographer to more quickly locate relevant image planes, making the imaging process more efficient.

In the embodiment illustrated in FIG. 5*c*, the current probe position is illustrated relative to the position on the representation of the breasts by the line 506. The image currently captured by the probe (e.g., live image 508) may be shown next to the representation of the body part. In some embodiments, the model, as described above is further trained, e.g., has a further output channel, to indicate the locations of lesions in the image. As an example, the You Only Look Once, YOLO, neural network may be suitable for real-time detection. Detected lesions may be encapsulated in boxes 510 (e.g., colored boxes) and/or labelled with scores indicating the certainty of the determination. In this way the lesions may be determined more quickly and reliably in a breast examination.

Turning now to other embodiments, generally, the processor may be caused to send an instruction to the probe to cause the probe to change to a different imaging mode if the indication received from the model indicates that the image comprises an image relevant to the medical diagnostic process. For example, if a relevant image is determined, the system may suggest the sonographer images the specific anatomy captured and (auto-)bookmarked by the system in additional ultrasound modes (e.g. Microflow imaging, Color Flow and/or Shear Wave Elastography amongst others). For example if a tumor is suspected on a given image, and activating Color mode will provide supplementary information for tumor diagnosis by studying the tumor vasculature. In such embodiments, the training data for the model may also contain a ground truth field corresponding to whether the imaging model should be changed and what mode it should be changed to, in order to train the model to suggest an imaging mode In one embodiment that combines some of the elements described above, once trained, the system 100 can be used in the inference mode in a clinic. In this embodiment, the system may be fed with live (e.g. real-time) ultrasound images and corresponding probe locations. Information on which images are manually saved by the user is also available to the system. A model is used to output a binary variable for each ultrasound image— "relevant" or "not relevant"-plus the probe pose (when and if available). If an image is deemed "not relevant", no action is taken. Otherwise, in this embodiment, the system will check if the user has already saved that image manually. If yes, no action is taken. If not, the system auto-saves that image. The auto-saved image may be kept in the buffer in case the sonographer subsequently bookmarks the same image (in order to avoid duplications). If no bookmarking action by the sonographer takes place within a threshold time interval, the system will add and save this frame to the auto-save list. A check may be performed via deep learning by pose regression and image redundancy verification with respect to those images already captured by the sonographer. The lists of manually-saved and auto-saved images are maintained and subsequently shown to the user separately, e.g. in grouped image boxes.

In this embodiment, the system 100 keeps monitoring and updating the manually-saved and auto-saved images. If the system auto-saves an image, it is possible that the sonographer may return to the same location and manually save an equivalent image at the same location after subsequent visual inspection. In such case if duplication is confirmed, the manually-saved image list may be updated accordingly, and the original auto-saved image may be deleted. Alternatively, the sonographer may be notified when an additional image is captured, including its location in the scanning area. This may prevent duplicated images from being saved and presented to the radiographer for subsequent review.

Image matching methods such as correlation, sum of difference, etc. may be combined with the probe position information to confirm whether an image is a duplicate.

Thus there is disclosed, various systems providing improved workflows for ultrasound systems. In clinical use, the systems described herein may generally augment current clinical workflows and improve diagnostic confidence by: (1) Tracking the actions of the sonographer during a given scan, including, but not limited to: live ultrasound images and corresponding probe locations during an ultrasound scan scan; Manually saved US images; and Probe positions corresponding to the manually saved images. (2) Automatically saving images deemed relevant by the system, if the image has not been previously saved manually by the user in the scanning session. (3) Display options may enable subsequent reviewers of the images, e.g. radiologists with the option to first review images archived by the sonographer and subsequently review auto-saved images. (4) The systems described herein may maintain complementary list of images in 'manually-saved' and 'automatically-saved' sections, in order to avoid redundancies. (5) Systems herein may further suggest sonographers to image the specific anatomy captured by auto-save with additional ultrasound modes (e.g. Microflow imaging, Color Flow and Shear Wave Elastography)

In addition, embodiments herein may be used for training purposes as it may be expected that the list of "uncaptured" images will be longer for novice users compared to more highly trained sonographers. The systems herein may thus improve ultrasound exam efficiency, providing more objective data for a first time right diagnosis and reducing time for procedures.

Figure 6:
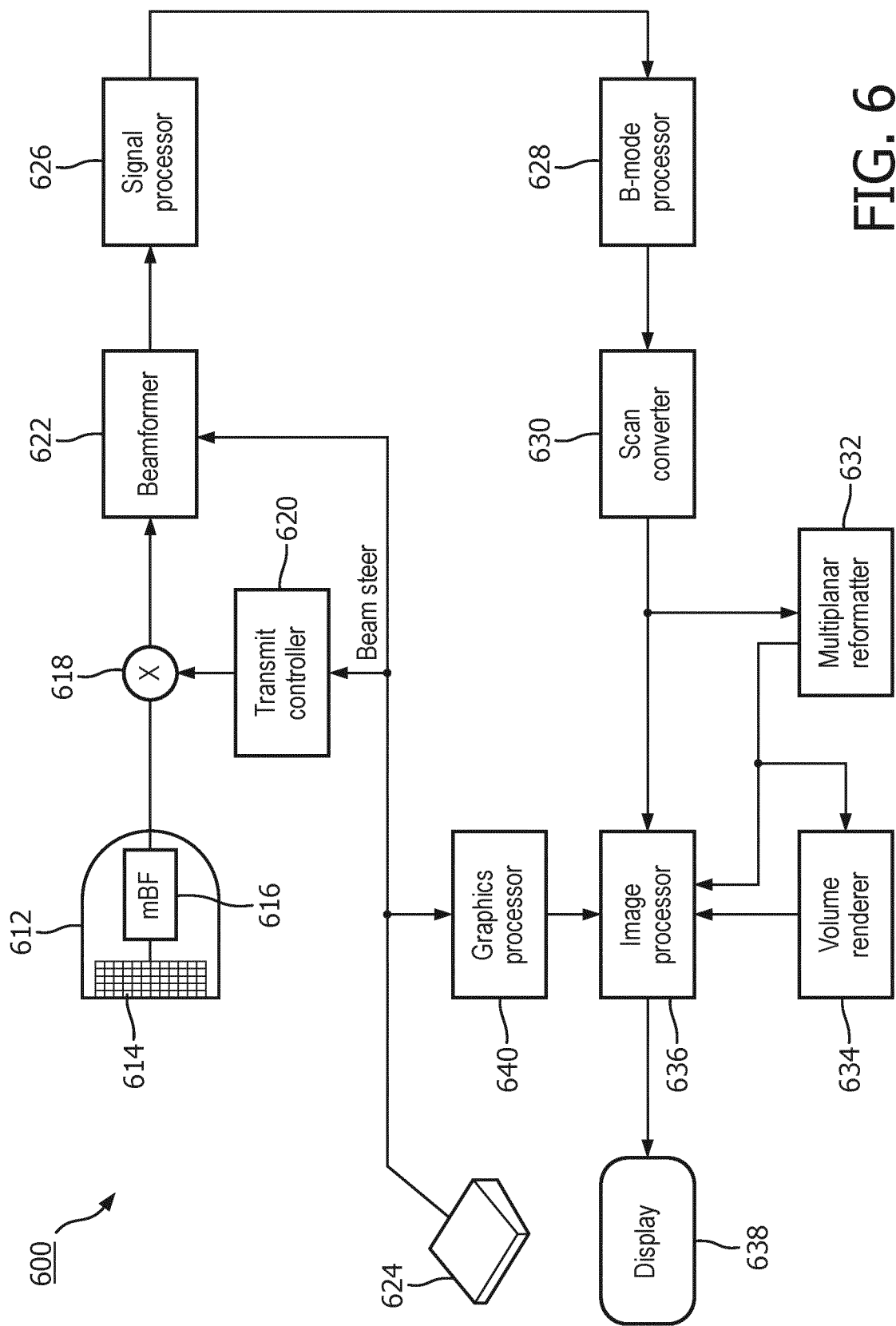
FIG. 6 illustrates an example system according to some embodiments herein.

Turning now to FIG. 6, FIG. 6 shows an example embodiment of an ultrasound system 600, constructed according to the principles described herein. One or more components shown in FIG. 6 may be included within a system configured to receive a data stream of two dimensional images taken using an ultrasound transducer, determine from the data stream that a feature of interest is in view of the transducer, trigger an alert to be sent to a user to indicate that the feature of interest is in view of the transducer, and send an instruction to the transducer to trigger the transducer to capture a three dimensional ultrasound image after a predetermined time interval.

For example, any of the above described functions of the processor 102 may be programmed, e.g., via computer executable instructions, into a processor of the system 600. The system 600 may further be programmed to perform the method 700 as described below. In some examples, the functions of the processor 102 or the method 700 may be implemented and/or controlled by one or more of the processing components shown in FIG. 6, including for example, the image processor 636.

In the ultrasound imaging system of FIG. 6, ultrasound probe 612 includes a transducer array 614 for transmitting ultrasonic waves into a region of the body and receiving echo information responsive to the transmitted waves. The transducer array 614 may be a matrix array that includes a plurality of transducer elements configured to be individually activated. In other embodiments, the transducer array 614 may comprise a one-dimensional linear array. The transducer array 614 is coupled to a micro-beamformer 616 in the probe 612 which may control the transmission and reception of signals by the transducer elements in the array. In the example shown, the micro-beamformer 616 is coupled by the probe cable to a transmit/receive (T/R) switch 618, which switches between transmission and reception and protects the main beamformer 622 from high energy transmit signals. In some embodiments, the T/R switch 618 and other elements in the system can be included in the transducer probe rather than in a separate ultrasound system base.

In some embodiments herein, ultrasound probe 612 may further comprise a motion detector, to detect motion of the probe, as described above.

The transmission of ultrasonic beams from the transducer array 616 under control of the microbeamformer 616 may be directed by the transmit controller 620 coupled to the T/R switch 618 and the beamformer 622, which receives input, e.g., from the user's operation of the user interface or control panel 624. One of the functions controlled by the transmit controller 620 is the direction in which beams are steered. Beams may be steered straight ahead from (orthogonal to) the transducer array, or at different angles for a wider field of view. The partially beamformed signals produced by the microbeamformer 616 are coupled to a main beamformer 622 where partially beamformed signals from individual patches of transducer elements are combined into a fully beamformed signal.

The beamformed signals are coupled to a signal processor 626. Signal processor 626 may process the received echo signals in various ways, such as bandpass filtering, decimation, I and Q component separation, and harmonic signal separation. Data generated by the different processing techniques employed by the signal processor 626 may be used by a data processor to identify internal structures, e.g., lesions in a breast, the ribs, or anatomical features of a neonate, and parameters thereof.

The signal processor 626 may also perform additional signal enhancement such as speckle reduction, signal compounding, and noise elimination. The processed signals may be coupled to a B-mode processor 628, which can employ amplitude detection for the imaging of structures in the body, including the ribs, the heart, and/or the pleural interface, for example. The signals produced by the B-mode processor are coupled to a scan converter 630 and a multiplanar reformatter 632. The scan converter 630 arranges the echo signals in the spatial relationship from which they were received in a desired image format. For instance, the scan converter 630 may arrange the echo signals into a two dimensional (2D) sector-shaped format. The multiplanar reformatter 632 can convert echoes which are received from points in a common plane in a volumetric region of the body into an ultrasonic image of that plane, as described in U.S. Pat. No. 6,443,896 (Detmer). A volume renderer 636 converts the echo signals of a 3D data set into a projected 3D image as viewed from a given reference point, e.g., as described in U.S. Pat. No. 6,530,885 (Entrekin et al).

The 2D or 3D images are coupled from the scan converter 630, multiplanar reformatter 632, and volume renderer 634 to an image processor 636 for further enhancement, buffering and temporary storage for display on an image display 638.

The graphics processor 640 can generate graphic overlays for display with the ultrasound images. These graphic overlays can contain, for example, a representation of a body part and/or an indication of the position of the probe when each ultrasound image in the subsequent real-time sequence of ultrasound images was captured, compared to the position of the probe when the image was captured, as was described with respect to FIG. 5.

Graphic overlays may further contain other information, for example, e.g., standard identifying information such as patient name, date and time of the image, imaging parameters, and the like. Graphic overlays may also include one or more signals indicating the target image frame has been obtained and/or the system 600 is in the process of identifying the target image frame. The graphics processor may receive input from the user interface 624, such as a typed patient name. The user interface 624 may also receive input prompting adjustments in the settings and/or parameters used by the system 600. The user interface can also be coupled to the multiplanar reformatter 632 for selection and control of a display of multiple multiplanar reformatted (MPR) images.

The skilled person will appreciate that the embodiment shown in FIG. 6 is an example only and that the ultrasound system 600 may also comprise additional components to those shown in FIG. 6, for example, such as a power supply or battery.

Figure 7:
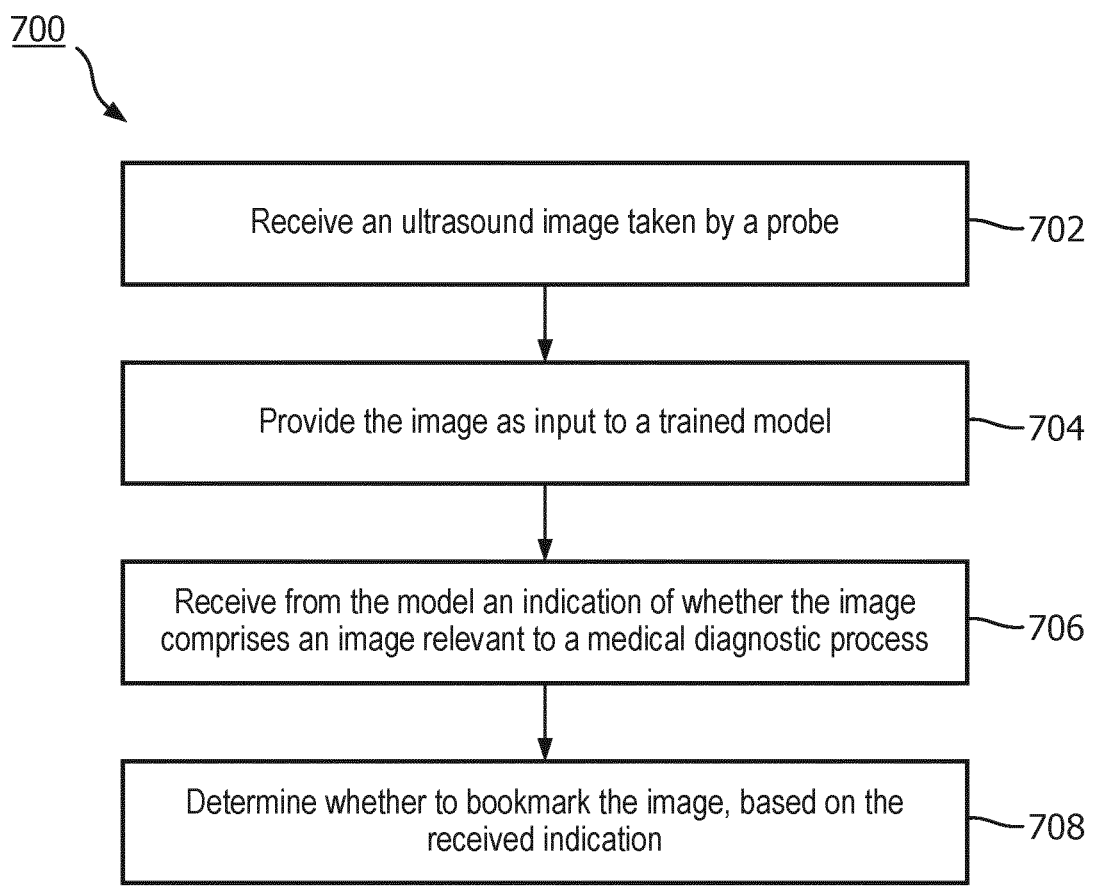
FIG. 7 illustrates an example method according to some embodiments herein.

Turning now to FIG. 7 in some embodiments there is a method 700 for obtaining medical ultrasound images. The method comprises: receiving 702 an ultrasound image; providing 704 the image as input to a trained model; receiving 706 from the model an indication of whether the image comprises an image relevant to a medical diagnostic process; and determining 708 whether to bookmark the image, based on the received indication.

Steps of receiving an ultrasound image; providing the image as input to a trained model; receiving from the model an indication of whether the image comprises an image relevant to a medical diagnostic process; and determining whether to bookmark the image, based on the received indication were all described above with respect to the system 100 and the details therein will be appreciated to apply equally to the method 700.

In some embodiments, there is also a method of training a machine learning model to predict whether an image comprises an image relevant to a medical diagnostic process. The method may be performed in addition, or separately to the method 700. The method comprises: providing training data to the machine learning model, the training data comprising: i) example ultrasound images; and ii) corresponding ground truth labels; wherein the ground truth labels indicate whether the image comprises an image relevant to the medical diagnostic process; and training the machine learning model to predict whether a new unseen image comprises an image relevant to the medical diagnostic process, based on the training data.

Training a model in this way was described in detail above with respect to the system 100 and the detail therein will be appreciated to apply equally to this method embodiment.

In another embodiment, there is provided a computer program product comprising a computer readable medium, the computer readable medium having computer readable code embodied therein, the computer readable code being configured such that, on execution by a suitable computer or processor, the computer or processor is caused to perform the method or methods described herein.

Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state

The invention claimed is:

1. A system for obtaining medical ultrasound images of a subject, the system comprising:
   a probe comprising an ultrasound transducer for capturing an ultrasound image;
   a memory comprising instruction data representing a set of instructions; and
   a processor configured to communicate with the memory and to execute the set of instructions, wherein the set of instructions, when executed by the processor, cause the processor to:
      receive an ultrasound image taken by the probe;
      provide the image as input to a trained model;
      receive from the model an indication of whether the image comprises an image relevant to a medical diagnostic process; and
      determine whether the image has been selected by a user as an image to be bookmarked;
   determine to bookmark the image if the image has not been selected by the user as an image to be bookmarked in response to the received indication from the trained model indicating that the image is relevant to the medical diagnostic process;
      send an instruction to a display to display the image to the user; and
      send an instruction to the display to indicate to the user whether the image has been i) selected by the user as an image to be bookmarked or ii) bookmarked by the system based on the received indication from the trained model.

2. A system as in claim 1 wherein the processor is further caused to: determine a location on a body of the subject associated with a position of the probe when the image was captured.

3. A system as in claim 2 wherein the processor is further caused to: send an instruction to the display to display an indication of the determined location on the body.

4. A system as in claim 3 wherein the processor is further caused to: send an instruction to the display to display a representation of a body part and overlay the indication of the determined location on the body over the representation of the body part.

5. A system as in claim 3 wherein the processor is further caused to: receive a subsequent real-time sequence of ultrasound images; and
   send an instruction to the display to display an indication of the position of the probe when each ultrasound image in the subsequent real-time sequence of ultrasound images was captured, compared to the position of the probe when the image was captured.

6. A system as in claim 2 wherein the set of instructions, when executed by the processor, further cause the processor to:
   provide the determined location on the body as a further input to the trained model; and
      wherein the trained model is further trained to provide the indication of whether the image comprises an image relevant to the medical diagnostic process based on the determined location.

7. A system as in claim 1 wherein the trained model has been trained to provide the indication of whether the image comprises an image relevant to the medical diagnostic process based on training data comprising: i) example ultrasound images and ii) corresponding ground truth indications of whether each example ultrasound image comprises an image relevant to the medical diagnostic process.

8. A system as in claim 1 wherein the set of instructions, when executed by the processor, further cause the processor to:
   send an instruction to the probe to cause the probe to change to a different imaging mode if the indication received from the model indicates that the image comprises an image relevant to the medical diagnostic process.

9. A system as in claim 1 wherein the set of instructions, when executed by the processor, further cause the processor to:
   suggest a further location to the user, for the user to perform a further scan, based on the indication received from the model.

10. A system as in claim 1 wherein the medical diagnostic process comprises a breast examination for determining a breast tissue anomaly.

11. A method for obtaining medical ultrasound images, the method comprising:
    receiving an ultrasound image;
    providing the image as input to a trained model;
    receiving from the model an indication of whether the image comprises an image relevant to a medical diagnostic process;
    determine whether the image has been selected by a user as an image to be bookmarked;
    determine to bookmark the image if the image has not been selected by the user as an image to be bookmarked in response to the received indication from the trained model indicating that the image is relevant to the medical diagnostic process;
       send an instruction to a display to display the image to the user; and
       send an instruction to the display to indicate to the user whether the image has been i) selected by the user as an image to be bookmarked or ii) bookmarked by the system based on the received indication from the trained model.

12. A computer program product comprising a non-transitory computer readable medium, the computer readable medium having computer readable code embodied therein, the computer readable code being configured such that, on execution by a suitable computer or processor, the computer or processor is caused to perform the method as claimed in claim 11.